United States Patent
Sun et al.

(10) Patent No.: US 9,709,543 B2
(45) Date of Patent: Jul. 18, 2017

(54) METHOD AND APPARATUS FOR DETERMINING NOX CONTENT IN AN EXHAUST GAS FEEDSTREAM OF AN INTERNAL COMBUSTION ENGINE

(71) Applicant: GM GLOBAL TECHNOLOGY OPERATIONS LLC, Detroit, MI (US)

(72) Inventors: Min Sun, Troy, MI (US); Shifang Li, Shelby Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 219 days.

(21) Appl. No.: 14/705,440

(22) Filed: May 6, 2015

(65) Prior Publication Data
US 2016/0327534 A1    Nov. 10, 2016

(51) Int. Cl.
*G01N 33/00* (2006.01)
*G01M 15/10* (2006.01)
*F01N 3/20* (2006.01)

(52) U.S. Cl.
CPC ....... *G01N 33/0037* (2013.01); *F01N 3/2066* (2013.01); *G01M 15/102* (2013.01)

(58) Field of Classification Search
CPC .................................................. G01N 33/0037
See application file for complete search history.

(56) References Cited

U.S. PATENT DOCUMENTS

| | | | | |
|---|---|---|---|---|
| 6,619,107 B1* | 9/2003 | Tsukamoto | ........ | G01N 33/0037 73/114.61 |
| 2004/0073381 A1* | 4/2004 | Ali | ...................... | G01N 33/0037 702/31 |
| 2016/0160785 A1* | 6/2016 | Basu | ...................... | F01N 3/208 701/104 |

* cited by examiner

Primary Examiner — Clayton E Laballe
Assistant Examiner — Dennis Hancock
(74) Attorney, Agent, or Firm — Quinn IP Law

(57) ABSTRACT

An internal combustion engine is described in conjunction with a method for dynamically determining a mass flow rate of nitrogen oxides (NOx) for its exhaust gas feedstream. The method includes determining a present engine operating point and determining a reference NOx content for a reference engine operating point. A combustion chemical reaction rate is determined based upon the present engine operating point and the reference engine operating point. A NOx content in the exhaust gas feedstream is dynamically determined during operation of the internal combustion engine based upon the reference NOx content, the combustion chemical reaction rate and a combustion mixing rate constant.

18 Claims, 1 Drawing Sheet

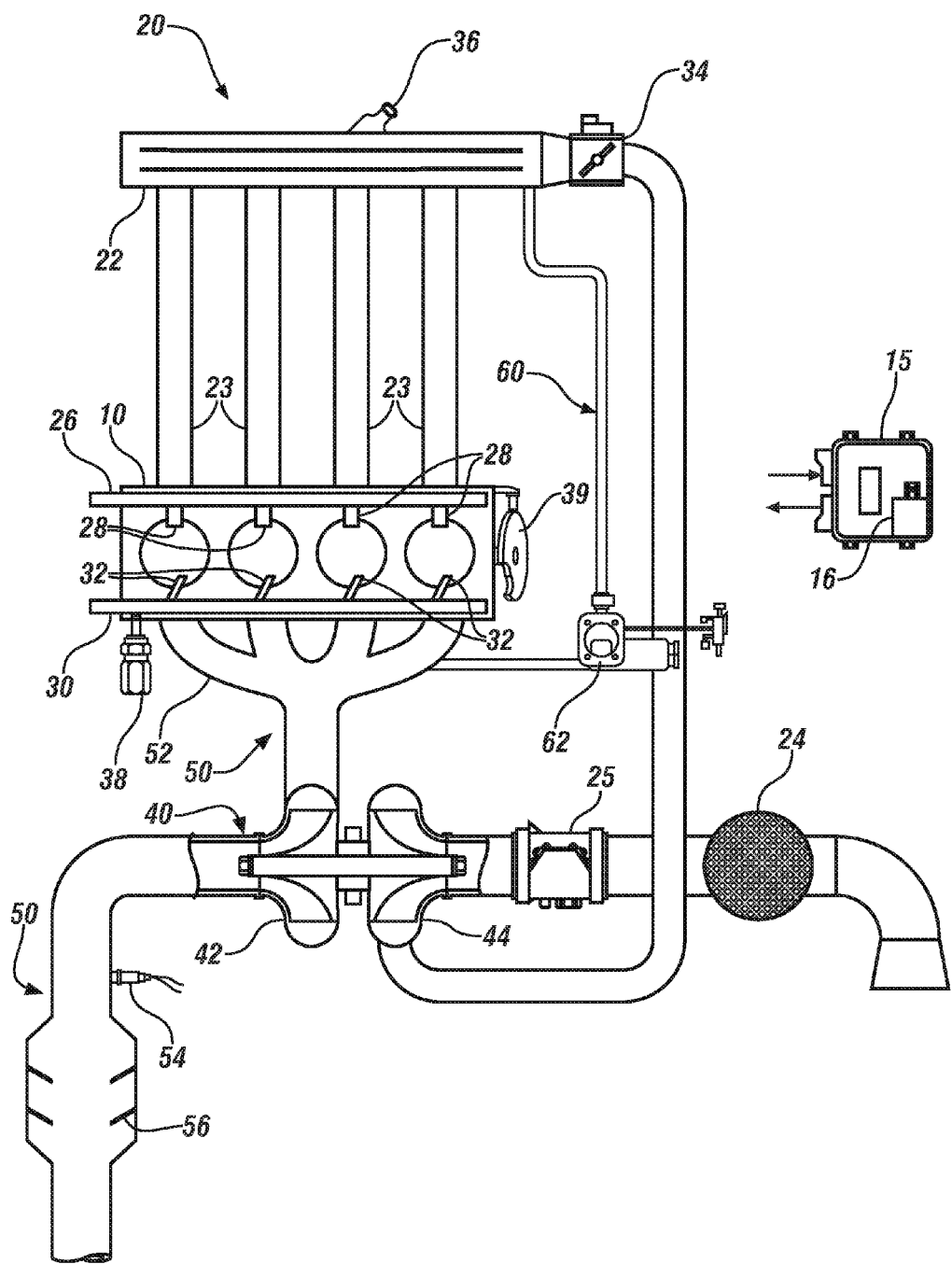

METHOD AND APPARATUS FOR DETERMINING NOX CONTENT IN AN EXHAUST GAS FEEDSTREAM OF AN INTERNAL COMBUSTION ENGINE

TECHNICAL FIELD

The disclosure generally relates to operation of an internal combustion engine, and determining nitrogen oxides (NOx) content in an exhaust gas feedstream of the internal combustion engine.

BACKGROUND

An internal combustion engine may couple to an exhaust aftertreatment system to purify an exhaust gas feedstream. An exemplary exhaust aftertreatment system may include purification devices such as oxidation catalysts, reduction catalysts and particulate filters. An exemplary exhaust aftertreatment system may include monitoring devices such as temperature sensors and exhaust gas constituent sensors. An engine controller may employ feedback from the monitoring devices to control operation of the internal combustion engine and to monitor operation of the internal combustion engine. One exhaust gas constituent sensor monitors nitrogen oxides (NOx) from the engine.

SUMMARY

An internal combustion engine is described in conjunction with a method for dynamically determining a mass flow rate of nitrogen oxides (NOx) for its exhaust gas feedstream. The method includes determining a present engine operating point and determining a reference NOx content for a reference engine operating point. A combustion chemical reaction rate is determined based upon the present engine operating point and the reference engine operating point. A NOx content in the exhaust gas feedstream is dynamically determined during operation of the internal combustion engine based upon the reference NOx content, the combustion chemical reaction rate and a combustion mixing rate constant.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying FIGURE, which schematically illustrates an internal combustion engine (engine) and accompanying engine controller in accordance with the disclosure.

DETAILED DESCRIPTION

Referring now to the drawing, wherein the depictions are for the purpose of illustrating certain exemplary embodiments only and not for the purpose of limiting the same, the FIGURE schematically illustrates an internal combustion engine (engine) 10 and accompanying engine controller 15 that have been constructed in accordance with this disclosure. The illustrated engine 10 is a compression-ignition engine configured to operate at an air/fuel ratio that is primarily lean of stoichiometry in one embodiment, although the disclosure is not so limited. The disclosure may be applied to any internal combustion engine system that monitors NOx emissions for purposes of engine control or diagnostics.

The illustrated engine 10 preferably includes a multi-cylinder direct-injection four-stroke internal combustion engine including an engine block, pistons, crankshaft, engine head, and other base engine components and systems. Specifically related to this disclosure, the engine 10 preferably has an air intake system 20, a fuel injection system 30, a swirl valve system 26, an intake air compressing system 40, an exhaust aftertreatment system 50 and an EGR system 60. The engine 10 operates in repetitively executed cycles, each including intake, compression, power and exhaust strokes. Engine operation may be monitored directly using sensors, or estimated using executable models and simulations, as described herein. One engine monitoring sensor includes an engine coolant temperature (ECT) sensor 38. Another engine monitoring sensor includes a crankshaft position sensor 39 for monitoring engine rotational speed (RPM) and piston position.

The air intake system 20 provides intake air to an intake manifold 22 that distributes and directs air into intake runners 23 leading to engine cylinders. The air intake system 20 has airflow ductwork and devices for monitoring and controlling the intake air flow. Devices for controlling the intake air flow include an intake air filter 24, a charge air cooler (when employed) and a throttle valve 34. The throttle valve 34 preferably includes an electronically controlled device that controls the intake airflow to the engine 10 in response to a control signal from the engine controller 15. The intake air compressing system 40 includes an intake air compressor 44 that is driven by an exhaust turbine 42 fluidly coupled to the exhaust system 50. Devices for monitoring the intake air flow preferably include a mass airflow sensor 25, which is preferably configured to monitor intake mass airflow (MAF), intake air temperature (IAT1, IAT2), air humidity (HUM) and inlet air pressure (IAP). The intake mass airflow (MAF) measured by the mass airflow sensor 25 may be employed to determine a measure of intake air/cylinder (APC). A pressure sensor 36 in the intake manifold 22 monitors manifold absolute pressure (MAP) and barometric pressure (BARO).

The fuel injection system 30 preferably includes a plurality of direct-injection fuel injectors 32 for supplying fuel directly into individual ones of the cylinders. In one embodiment, a common rail fuel system supplies pressurized fuel to all the fuel injectors 32. In one embodiment, the fuel injectors 32 are solenoid-activated devices that are controlled by a command signal originating from the controller 15. The fuel injectors 32 are capable of executing multiple fuel injection events during each cylinder event. The multiple fuel injection events may include executing one or more pilot injection events during the intake stroke or early in the compression stroke and executing one or more main injection events late in the compression stroke. A mass of fuel delivered to the cylinders during each cylinder event may be employed to indicate engine load.

The swirl valve system 26 may include a plurality of controllable swirl valves 28 that are located in the intake runners 23 leading to the cylinders. In one embodiment, each of the swirl valves 28 is a controllable butterfly valve that has an outside diameter that is less than the inside diameter of the intake runner 23. In one embodiment, the swirl valves 28 are controlled to a completely closed state at engine idle conditions to induce turbulence in the flow of intake air into each of the cylinders, thus improving in-cylinder fuel and air mixing. The swirl valves 28 are increasingly opened with increased engine speed in response to a command that may originate from the controller 15. Other embodiments of controllable swirl valves 28 may be employed with similar effect.

An exhaust manifold 52 entrains exhaust gases output from the engine 10 for channeling through the exhaust turbine 42 of the intake air compressing system 40 to the exhaust aftertreatment system 50. An exhaust gas recirculation (EGR) system 60 recirculates a portion of the exhaust gases to the intake manifold 20 through a flow control valve referred to as an EGR valve 62. The EGR system 60 may include, e.g., an EGR cooler, a bypass valve and related sensors. The engine controller 15 controls mass flow of exhaust gas to the intake manifold 22 by controlling opening of the EGR valve 62. The EGR system 60 and related control systems are known.

The exhaust aftertreatment system 50 includes one or a plurality of exhaust purification devices 56 and one or a plurality of exhaust gas sensors 54. The exhaust purification devices 56 may include, by way of example, an oxidation catalyst, a particulate filter and a selective catalyst reduction device when the engine 10 is configured as a compression-ignition engine. The exhaust gas sensors 54 may include, by way of example, an engine-out NOx sensor, a wide-range air/fuel ratio sensor, and one or a plurality of temperature sensors.

The terms controller, control module, module, control, control unit, processor and similar terms refer to any one or various combinations of Application Specific Integrated Circuit(s) (ASIC), electronic circuit(s), central processing unit(s), e.g., microprocessor(s) and associated memory and storage devices (read only, programmable read only, random access, hard drive, etc.) executing one or more software or firmware programs or routines, combinational logic circuit(s), input/output circuit(s) and devices, signal conditioning and buffer circuitry and other components to provide a described functionality. Software, firmware, programs, instructions, control routines, code, algorithms and similar terms mean any controller-executable instruction sets including calibrations and look-up tables. Each controller executes control routine(s) to provide desired functions, including monitoring inputs from sensing devices and other networked controllers and executing control and diagnostic routines to control operation of actuators. Routines may be executed at regular intervals, for example each 100 microseconds or 3.125, 6.25, 12.5, 25 and 100 milliseconds during ongoing operation. Alternatively, routines may be executed in response to occurrence of an event. Communications between controllers and between controllers, actuators and/or sensors may be accomplished using a direct wired link, a networked communications bus link, a wireless link or any another suitable communications link. The term 'model' refers to a processor-based or processor-executable code and associated calibration that simulates a physical existence of a device or a physical process.

The engine controller 15 preferably includes an executable control routine 16 for dynamically determining a measure of nitrogen oxides (NOx), e.g., in parts per million (ppm) or another suitable metric, for the exhaust gas feedstream that is produced by the engine 10. As used herein, the terms 'dynamic' and 'dynamically' describe steps or processes that are executed in real-time and are characterized by monitoring or otherwise determining states of parameters and regularly or periodically updating the states of the parameters during execution of a routine or between iterations of execution of the routine. As used herein, the term 'engine-specific' indicates a specific model of an engine produced by a manufacturer, and preferably relates to elements such as cylinder configuration, fuel delivery and others.

The control routine 16 includes a physics-based determination of NOx that employs engine configuration-specific estimates of chemical reaction rates and a combustion mixing rate constant (C) using presently observed states of engine operating parameters. The control routine 16 includes the following equation that is reduced to executable code that is periodically executed to determine NOx concentration in the exhaust gas feedstream based upon monitored states of engine parameters.

$$NO_x = \frac{C\left(NO'_{x_{ref}}\left(\frac{APC}{APC_{ref}}\right)^{g1} e^{g2+...+g11}\right)}{C + \left(NO'_{x_{ref}}\left(\frac{APC}{APC_{ref}}\right)^{g1} e^{g2+...+g11}\right)} \quad [1]$$

EQ. 1 may be executed to dynamically determine NOx in the exhaust gas feedstream that is produced by the engine 10 for a present engine speed/load operating point based upon a reference NOx content, a combustion chemical reaction rate and a combustion mixing rate constant, wherein the combustion chemical reaction rate is determined based upon an air per cylinder term and a reaction rate term. The terms of EQ. 1 relate to engine parameters for a present engine speed/load operating point and a reference engine speed/load operating point. The NOx state calculated by execution of EQ. 1 as part of the control routine 16 is based upon the reference NOx content term $NO_{x_{ref}}'$, a mixing rate constant C and a plurality of differential terms g2 through g11 that characterize deviations from the reference speed/load operating point. As such, execution of EQ. 1 has an upper bound stability.

The reference NOx content term $NO_{x_{ref}}'$ is the concentration of nitrogen oxides in the flow of exhaust gas that the engine 10 produces while operating at the reference state. The reference engine speed/load operating point may be any specific operating point of the engine 10, preferably under steady state operating conditions and at defined operating parameters. By way of example, the reference engine speed/load operating point may include an engine idle condition with all of the various operating parameters of the engine 10 being set at pre-defined limits or rates. Alternatively or in addition, there may be a plurality of engine speed/load operating points over the ranges of engine speeds between idle and a maximum engine speed and ranges of engine loads between idle and a maximum engine load. The term C of EQ. 1 is an engine-specific mixing rate constant representing an upper limit or maximum kinetic reaction rate that is due to fuel and air mixing. The combustion chemical reaction rate portion of EQ. 1 provides a model reaction rate term that includes the air per cylinder term and the reaction rate term as follows:

$$\left(\frac{APC}{APC_{ref}}\right)^{g1} e^{g2+...+g11}$$

The air per cylinder term is as follows:

$$\left(\frac{APC}{APC_{ref}}\right)$$

wherein APC is a measure of intake air per cylinder for the present engine speed/load operating point, and $APC_{ref}$ is an intake air per cylinder for the reference engine speed/load operating point.

The $g_1$ term is determined as follows:

$$g_1 = k_1 e^{C \Delta injT}$$

wherein e is the base of the natural logarithm, the term $\Delta injT$ is a fuel injection timing differential from a nominal fuel injection timing, the term c is an engine-specific constant term and $k_1$ is an engine-specific scalar factor that can be derived for each of a plurality of engine speed/load operating points over a range of achievable engine/speed operating points.

The reaction rate term is as follows:

$$e^{g_2 + \cdots + g_{11}}$$

wherein:
e is the base of the natural logarithm;
$g_2 = k_2 \Delta P_{inj}$;
$g_3 = k_3 \Delta injT$;

$$g_4 = k_4 \Delta O_{2_{int_{pct}}};$$

$g_5 = k_5 \Delta T_{int}$;
$g_6 = k_6 \Delta Pct_{swirl}$;
$g_7 = k_7 \Delta T_{cool}$;
$g_8 = k_8 \Delta T\_R_{1_{pilot}}$;
$g_9 = k_9 \Delta T\_R_{2_{pilot}}$;
$g_{10} = k_{10} \cdot \Delta M\_R_{1_{pilot}}$; and
$g_{11} = k_{11} \Delta M\_R_{2_{pilot}}$;

The term $NO_{x_{ref}}$ is a reference NOx content, e.g., a concentration, in ppm (parts per million) for the reference engine speed/load operating point.

The term $\Delta P_{inj}$ is a fuel injection pressure differential from a fuel injection pressure for the reference engine speed/load operating point.

The term $\Delta T_{cool}$ is an engine coolant temperature differential from an engine coolant temperature for the reference engine speed/load operating point.

The term $\Delta T_{int}$ is an intake air temperature differential from an intake air temperature for the reference engine speed/load operating point.

The term $$\Delta O_{2_{int_{pct}}}$$

is a differential in oxygen concentration, in percent, for intake air from an oxygen concentration for intake air for the reference engine speed/load operating point.

The term $\Delta Pct_{swirl}$ is a differential in commanded intake air swirl, in percent, from a commanded intake air swirl for the reference engine speed/load operating point.

The term $\Delta T\_R_{1_{pilot}}$ is a fuel injection timing differential from a fuel injection timing for a first pilot fuel injection for the reference engine speed/load operating point.

The term $$\Delta M\_R_{1_{pilot}}$$

is a fuel injection mass differential from a fuel injection mass for the first pilot fuel injection for the reference engine speed/load operating point.

The term $\Delta T\_R_{2_{pilot}}$ is a fuel injection timing differential from a fuel injection timing for a second pilot fuel injection for the reference engine speed/load operating point.

The term $\Delta M\_R_{2_{pilot}}$ is a fuel injection mass differential from a fuel injection mass for a the second pilot fuel injection for the reference engine speed/load operating point.

The terms $k_2$, $k_3$, $k_4$, $k_5$, $k_6$, $k_7$, $k_8$, $k_9$, $k_{10}$ and $k_{11}$ are engine-specific scalar factors. In one embodiment, the terms $k_1$-$k_{11}$ are engine-specific scalar factors that can be derived for each of a plurality of engine speed/load operating points over a range of achievable engine/speed operating points.

The NOx state calculated by execution of EQ. 1 is derived based on physics concepts related to temperature, flow and mixing, and also related to chemical reaction rates. Hence, values for the engine-specific scalar factors $k_1$-$k_{11}$ may be readily populated and stored in calibration tables in memory devices connected to the controller 15. Calibration exercises to determine the engine-specific scalar factors $k_1$-$k_{11}$ may be conducted with designed-experiment (DOE) methodologies and optimization software and tools to determine specific values.

The NOx state calculated by execution of EQ. 1 in the controller 15 may be employed to monitor performance of the exhaust gas sensor 54 when the exhaust gas sensor 54 is configured to monitor engine-out NOx emissions, thus providing a second indicator of the engine-out NOx emissions for purposes of diagnostics. The NOx state calculated by execution of EQ. 1 in the controller 15 may be employed to monitor engine-out NOx emissions, thus providing an indicator of the engine-out NOx emissions for purposes of engine control. The exhaust gas sensor 54 in such configurations may be configured to only monitor air/fuel ratio in the exhaust gas feedstream.

The detailed description and the drawings or FIGURES are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:
1. A method for determining a measure of nitrogen oxides (NOx) in an exhaust gas feedstream produced by an internal combustion engine, the method comprising:
   determining, by a controller, a present engine operating point;
   determining a reference NOx content for a reference engine operating point;
   determining a combustion chemical reaction rate based upon the present engine operating point and the reference engine operating point;
   dynamically determining NOx content in the exhaust gas feedstream during operation of the internal combustion engine based upon the reference NOx content, the combustion chemical reaction rate and a combustion mixing rate constant; and controlling, via the controller, operation of the internal combustion engine based upon the determined NOx content in the exhaust gas feedstream.

2. The method of claim 1, wherein determining the combustion chemical reaction rate based upon the present engine operating point and the reference engine operating point comprises:

determining an air per cylinder term based upon the present engine operating point and the reference engine operating point;

determining a reaction rate term based upon the present engine operating point and the reference engine operating point; and determining the combustion chemical reaction rate based upon the air per cylinder term and the reaction rate term.

3. The method of claim 2, wherein determining the reaction rate term based upon the present engine operating point and the reference engine operating point further comprises:

dynamically determining present states of a plurality of engine parameters for the present engine operating point;

determining a plurality of reference factors for the reference engine operating point;

determining a plurality of reaction elements for the plurality of reference factors and the present states of the engine parameters; and determining the reaction rate term based upon the reaction elements.

4. The method of claim 3, wherein determining a plurality of reaction elements for the plurality of reference factors and the present states of the engine parameters comprises determining one of the reaction elements for one of the reference factors based upon a difference between a present fuel injection timing and a reference fuel injection timing associated with the reference engine operating point.

5. The method of claim 3, wherein determining a plurality of reaction elements for the plurality of reference factors and the present states of the engine parameters comprises determining one of the reaction elements for one of the reference factors based upon a difference between a present fuel injection pressure and a reference fuel injection pressure associated with the reference engine operating point.

6. The method of claim 3, wherein determining a plurality of reaction elements for the plurality of reference factors and the present states of the engine parameters comprises determining one of the reaction elements for one of the reference factors based upon a difference between a present intake oxygen concentration and a reference intake oxygen concentration associated with the reference engine operating point.

7. The method of claim 3, wherein determining a plurality of reaction elements for the plurality of reference factors and the present states of the engine parameters comprises determining one of the reaction elements for one of the reference factors based upon a difference between a present intake air temperature and a reference intake air temperature associated with the reference engine operating point.

8. The method of claim 3, wherein determining a plurality of reaction elements for the plurality of reference factors and the present states of the engine parameters comprises determining one of the reaction elements for one of the reference factors based upon a difference between a present intake air swirl command and a reference intake air swirl command associated with the reference engine operating point.

9. The method of claim 3, wherein determining a plurality of reaction elements for the plurality of reference factors and the present states of the engine parameters comprises determining one of the reaction elements for one of the reference factors based upon a difference between a present engine temperature and a reference engine temperature associated with the reference engine operating point.

10. The method of claim 3, wherein determining a plurality of reaction elements for the plurality of reference factors and the present states of the engine parameters comprises determining one of the reaction elements for one of the reference factors based upon a difference between a present pilot fuel injection mass and a reference pilot fuel injection mass associated with the reference engine operating point.

11. The method of claim 3, wherein determining a plurality of reaction elements for the plurality of reference factors and the present states of the engine parameters comprises determining one of the reaction elements for one of the reference factors based upon a difference between a present pilot fuel injection timing and a reference pilot fuel injection timing associated with the reference engine operating point.

12. The method of claim 6, wherein controlling operation of the internal combustion engine based upon the NOx content in the exhaust gas feedstream comprises monitoring performance of an exhaust gas sensor based upon the NOx content in the exhaust gas feedstream.

13. The method of claim 6, wherein controlling operation of the internal combustion engine based upon the NOx content in the exhaust gas feedstream comprises employing the dynamically determined NOx content in the exhaust gas feedstream as an indicator of the engine-out NOx emissions for purposes of diagnostics.

14. An internal combustion engine, comprising:

an air intake system, a fuel injection system, an exhaust aftertreatment system, and an engine controller;

the engine controller including a control routine for determining a measure of nitrogen oxides (NOx) in an exhaust gas feedstream produced by the internal combustion engine upstream of the exhaust aftertreatment system, the control routine including the following executable steps:

determine a present engine operating point;

determine a reference NOx content for a reference engine operating point;

determine a combustion chemical reaction rate based upon the present engine operating point and the reference engine operating point;

dynamically determine NOx content in the exhaust gas feedstream during operation of the internal combustion engine based upon the reference NOx content, the combustion chemical reaction rate and a combustion mixing rate constant; and control operation of the internal combustion engine based upon the determined NOx content in the exhaust gas feedstream.

15. The internal combustion engine of claim 14, wherein the control routine including the executable step to determine the combustion chemical reaction rate based upon the present engine operating point and the reference engine operating point comprises the control routine including the following executable steps:

determine an air per cylinder term based upon the present engine operating point and the reference engine operating point;

determine a reaction rate term based upon the present engine operating point and the reference engine operating point; and determine the combustion chemical reaction rate based upon the air per cylinder term and the reaction rate term.

16. The internal combustion engine of claim 15, wherein the control routine including the executable step to determine the reaction rate term based upon the present engine operating point and the reference engine operating point further comprises a control routine including the following executable steps:

dynamically determine present states of a plurality of engine parameters for the present engine operating point;

determine a plurality of reference factors for the reference engine operating point;

determine a plurality of reaction elements for the plurality of reference factors and the present states of the engine parameters; and determine the reaction rate term based upon the reaction elements.

17. The internal combustion engine of claim 14, wherein the internal combustion engine further comprises an exhaust gas sensor disposed to monitor the exhaust gas feedstream; and wherein the control routine includes the executable step to monitor performance of the exhaust gas sensor based upon the NOx content in the exhaust gas feedstream.

18. The internal combustion engine of claim 14, wherein the dynamically determined NOx content in the exhaust gas feedstream provides an indicator of the engine-out NOx emissions for purposes of diagnostics.

* * * * *